United States Patent [19]
Davis et al.

[11] B  3,981,929
[45] Sept. 21, 1976

[54] METHOD OF SEPARATING METHYLOLPHENOLS FROM SOLUTIONS

[75] Inventors: Robert Elliott Davis, Oklahoma City, Okla.; Friedrich Josef Weck, Hacienda Heights, Calif.

[73] Assignee: Kerr-McGee Corporation, Oklahoma City, Okla.

[22] Filed: May 16, 1974

[21] Appl. No.: 470,348

[44] Published under the second Trial Voluntary Protest Program on January 13, 1976 as document No. B 470,348.

Related U.S. Application Data

[63] Continuation-in-part of Ser. Nos. 716,337, March 27, 1968, abandoned, and Ser. No. 321,046, Jan. 4, 1973, abandoned.

[52] U.S. Cl. .................. 260/621 K; 260/623 R; 260/624 A; 260/627 G; 260/620
[51] Int. Cl.² .................. C07C 39/06; C07C 39/27
[58] Field of Search........ 260/627 G, 624 A, 621 A, 260/621 K, 623 R, 620, 621, 621 B

[56]          References Cited
         UNITED STATES PATENTS

| | | | |
|---|---|---|---|
| 2,260,337 | 10/1941 | Prescott et al. | 260/624 A |
| 2,260,338 | 10/1941 | Prescott et al. | 260/624 A |
| 2,587,753 | 4/1952 | O'Conner | 260/621 A |
| 2,899,470 | 8/1959 | Goldstein et al. | 260/624 A |
| 3,479,294 | 11/1967 | Week | 252/182 |

*Primary Examiner*—James O. Thomas, Jr.
*Assistant Examiner*—W. B. Lone
*Attorney, Agent, or Firm*—William G. Addison

[57]          ABSTRACT

A method of separating methylolphenols from an organic solution containing the methylolphenols by contacting the organic solution with an aqueous alkaline borate solution in which lithium ions are present in a quantity greater than any other single alkali metal ion for a period of time sufficient to form a solid complex of the lithium and boron with the methylolphenols which then are separated from the organic solution.

The methylolphenols subsequently may be recovered from the complex by decomposing the complex with acid and dissolving the released methylolphenols in an organic solvent.

9 Claims, No Drawings

METHOD OF SEPARATING METHYLOLPHENOLS FROM SOLUTIONS

This application is a continuation-in-part of application Ser. No. 716,337, filed Mar. 27, 1968, now abandoned, and application Ser. No. 321,046, filed Jan. 4, 1973, now abandoned.

BACKGROUND OF THE INVENTION

This invention relates to the separation of methylolphenols from an organic solution. More particularly, the invention relates to the method of selectively separating methylolphenols from a solution containing the methylolphenols together with phenolic impurities.

Methylolphenols, also known as saligenins and hydroxybenzyl alcohols, have a number of commercial uses. For example, it has been known for many years that methylolphenols are intermediates in the production of phenolic resins. In recent years, methylolphenols have been disclosed to be useful as extractants for recovering boron values from boron-containing brines and for reducing the boron content of oil well brines, irrigation water and the like.

Methylolphenols may be prepared by a number of different methods such as, for example, the condensation reaction of a phenol with formaldehyde, the reduction of a salicylaldehyde by means of sodium amalgam, hydrogenation of salicylaldehydes over platinum black and the like. However, during the preparation of the methylolphenols, phenolic compounds other than the desired methylolphenols may also be formed and recovered with the desired product. In addition, methylolphenols are sensitive to heat and acid conditions with the result that the methylolphenols, when subjected to certain conditions during storage and/or use, tend to dimerize to form bis-phenols such as dibenzyl ethers and methylene dimers.

Generally, it is preferred to remove both the phenolic impurities formed during preparation of the methylolphenols and the bis-phenols which may form during storage or use of the methylolphenols, since their presence tends to adversely affect the properties and function of the methylolphenols. A number of techniques, such as selective leaching with organic solvents, chemical and adsorbent treatment and the like have been suggested heretofore for removing these phenolic impurities. However, these prior techniques are relatively complex, inefficient, or ineffective or they suffer from other disadvantages making their use less than completely satisfactory in a commercial operation.

SUMMARY OF THE INVENTION

The present invention provides a method for separating methylolphenols from an organic solution containing the methylolphenols. The methylolphenols are precipitated from the solution as a solid lithium-boron-methylolphenol complex by contacting the solution with an aqueous alkaline borate solution containing lithium ions. Phenolic impurities, such as bis-phenols which may be present in the solution are not precipitated in the complex so that a selective separation of the methylolphenol from such impurities is thereby effected.

The solid complex thus formed is separated from the solution and subsequently may be treated to recover substantially pure methylolphenol or to form a solution of the methylolphenol which is relatively free of phenolic impurities. Thus, up to about 90% of the methylolphenol values in the impure solution are recovered and up to about 90% of the phenolic impurities are removed to provide substantially pure methylolphenol. It will be understood that the term "phenolic impurities" as used in the present specification and claims includes phenolic compounds, other than methylolphenols, such as bis-phenols which may be formed during preparation of the methylolphenol or during storage, handling, and/or use of the methylolphenol.

DESCRIPTION OF THE PREFERRED EMBODIMENTS

The present invention is based on the discovery that an aqueous alkaline borate solution containing lithium ions will selectively complex methylolphenol values from an organic solution of the methylolphenol.

In one embodiment, this invention comprises treating an organic solution of methylolphenol with an aqueous alkaline borate solution containing lithium ions, allowing a solid lithium-boron-methylolphenol complex to form and recovering the solid complex from the solution. The complex thus formed is believed to be $LiBO_2 \cdot (X)_2 \cdot n\, H_2O$ in which X is a methylolphenol and $n$ ranges from 1 to 6. This method provides a rapid, complete and selective process for recovering methylolphenols from an organic solution thereof while simultaneously separating said methylolphenols from any phenolic impurities which also may have been present in the solution.

The methylolphenols to which the present invention is applicable have the formula:

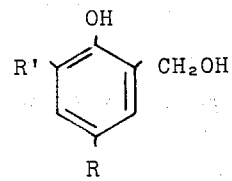

in which R is selected from the group consisting of hydrogen, phenyl, halogen and alkyl radicals having from 1 to 8 carbon atoms and R' is selected from the group consisting of hydrogen, phenyl, halogen, $CH_2OH$ and alkyl radicals having from 1 to 15 carbon atoms.

The preferred methylolphenols are those in which R is selected from the group consisting of hydrogen, phenyl, bromine, chlorine and alkyl radicals having from 3 to 8 carbon atoms and R' is selected from the group consisting of phenyl, chloro, $CH_2OH$ and alkyl radicals having from 1 to 9 carbon atoms. Such methylolphenols include, for example, 4-octyl-2,6-dimethylolphenol;
2-chloro-4-(1,1,3,3-tetramethyl butyl)-6-methylolphenol;
2,4-dichloro-6-methylolphenol;
2-chloro-4-tertiary-butyl-6-methylolphenol;
2-bromo-4-tertiary-butyl-6-methylolphenol;
2-chloro-4-phenyl-6-methylolphenol;
2-bromo-4-phenyl-6-methylolphenol;
2-bromo-4-isooctyl-6-methylolphenol;
2-methyl-4-tertiary-butyl-6-methylolphenol;
2,4-di(tertiary-amyl)-6-methylolphenol;
2-phenyl-4-methyl-6-methylolphenol;
2,4-di(sec.-amyl)-6-methylolphenol;

4-phenyl-2,6-dimethylolphenol;
2-cyclohexyl-4-chloro-6-methylolphenol;
2-methylolphenol.

The methylolphenols, as generally prepared and as available commercially, usually contain about 0% to about 50% phenolic impurities. The term "phenolic impurity" as used herein is defined as the unreacted or partially reacted starting materials, by-products of the reaction and degradation products of a methylolphenol produced by a process selected from the group consisting of condensing a phenol with formaldehyde and reducing a salicylaldehyde. The phenolic impurity will always include at least one of the following:

a. unreacted starting materials having the formula

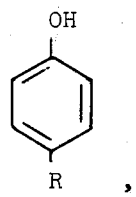

b. partially reacted starting materials having the formula

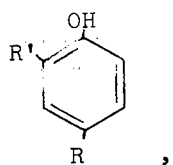

c. degradation products of the methylolphenol having the formula

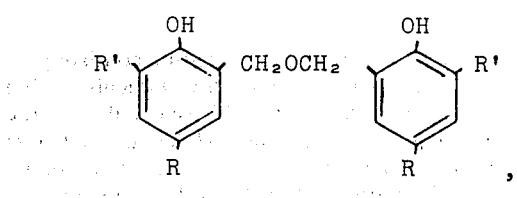

and d. degradation products of the methylolphenol having the formula

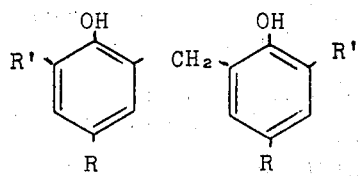

in which the R and R' in each instance are as hereinbefore defined for the methylolphenol.

As those versed in the art will appreciate the particular organic solvent utilized is not critical. Generally, any of those organic solvents used in a liquid-liquid solvent extraction process are suitable. Obviously, of course, the solvent must be substantially inert with respect to the methylolphenol, must be one in which the methylolphenol is soluble and in which the solid complex of lithium and boron with said methylolphenol has limited solubility. Examples of such solvents include aromatic hydrocarbons such as benzene, toluene, xylenes and alkyl benzene and the like; aliphatic hydrocarbons such as hexane, heptane, octane, nonane, kerosene, mineral spirits, petroleum ether and the like; dialkyl ethers such as butyl ether, isopropyl ether, hexyl ether and the like; chlorinated hydrocarbons such as chloroform, carbon tetrachloride, chlorobenzene and the like; and monohydric alcohols having from 8 to 17 carbon atoms per molecule. Mixtures of the foregoing solvents are suitable for use in accordance with the present invention. Generally, kerosene or aliphatic hydrocarbons are preferred.

The concentration of methylolphenol in the organic solution to be treated may vary widely. Thus, organic solutions containing as low as about 1% or as high as about 50% or more methylolphenol may be treated according to the present invention. Generally, the organic solution contains from about 1% to about 20% by weight of methylolphenol, from about 1% to about 20% by weight phenolic impurities and from about 60% to about 98% by weight of the organic solvent. Excellent results have been obtained when a solution containing from about 5% to about 15% by weight methylolphenol, about 5% to about 15% by weight phenolic impurities and about 70% to about 90% by weight of solvent were treated according to the present invention.

The aqueous alkaline borate solution which is contacted with the methylolphenol solution contains lithium ions as the predominant alkali metal ions and has a lithium-to-boron atomic ratio of at least about one. More particularly, the aqueous alkaline borate solution should contain more lithium ions that any other single alkali metal ion and preferably more lithium ions than all other alkali metal ions. Generally, it is preferred that substantial amounts of alkali metal ions other than lithium ions not be present in the aqueous solutions, because the presence of substantial amounts of alkali metals other than lithium retards or inhibits the rapid formation of the methylolphenol complex. Therefore, in a preferred embodiment of the present invention, the aqueous alkaline borate solution is substantially free of such other alkali metal ions.

The lithium and boron values required in the aqueous solution to form the solid complex may be provided by dissolving a lithium borate, such as lithium metaborate or lithium tetraborate, in water. Alternatively, a source of lithium ions such as lithium hydroxide, lithium carbonate, lithium sulfate and the like and a source of boron ions such as boric acid, boric oxide and the like may be introduced separately into water to provide the aqueous complexing solutions. Preferably, the aqueous complexing solution has a lithium to boron ratio of about 1. Generally, it is preferred to use an aqueous solution of lithium metaborate as the complexing solution.

The concentration of lithium and boron ions in the aqueous solution should be sufficient to provide at least about one lithium ion and one boron ion for every two moles of methylolphenol in the organic solution. Higher concentrations of lithium and boron may, of course, be used. Lesser concentrations of lithium and boron in the aqueous solution, however, are effective in complexing only a portion of the methylolphenol.

It has been found that when an aqueous solution of lithium metaborate is used as the complexing solution about 90% or more of the methylolphenol contained in an impure organic methylolphenol solution may be recovered when the lithium metaborate to methylolphenol ratio in the system is between about 0.5 to about 1. However, when this ratio is below about 0.5, only about 50% to about 70% of the methylolphenol is complexed and precipitated out of solution. Lithium metaborate solutions having a concentration of between about 0.2 and about 1.0 molar, and preferably about 0.5 molar, have been found to be particularly effective in forming the complex.

In the practice of this invention an organic solution of methylolphenol, which may contain phenolic impurities, is contacted with an aqueous lithium-boron-containing solution, with agitation, until a solid complex forms throughout the organic layer. Formation of the solid complex usually occurs within about 0.5 hour, but longer periods of time may sometimes be required. Since, as discussed above, the presence in the extraction system of alkali metal ions other than lithium tends to retard or inhibit formation of the complex, it generally is preferred to treat the methylolphenol solution to remove such other alkali metal ions therefrom prior to contacting the organic solution with the aqueous complexing solution. Such alkali metal ions are effectively stripped from the methylolphenol solution by contacting the organic solution with a dilute inorganic acid, such as about 0.1N to about 1N sulfuric acid.

After formation of the solid complex is complete, the complex is separated and recovered from the organic layer by any suitable means such as filtration or the like. The complex thus recovered is believed to have the composition $LiBO_2 \cdot (X)_2 \cdot n\ H_2O$ in which X is the methylolphenol and $n$ ranges from about 1 to 6.

This complex has utility as a gasoline additive and may be used in this form. Thus, the complex may be added to gasoline together with tetraethyl lead or tetramethyl lead and a halide scavenging agent. The boron values present in the complex serve to eliminate the adverse effects of the lead deposits which form in gasoline to which tetraethyl and tetramethyl lead has been added to thereby improve the preignition characteristics of the gasoline. The complex may be added in the amount of between about 0.002% and about 0.1% boron based on the gasoline weight.

The methylolphenol may be recovered from the complex by decomposing the complex with a dilute mineral acid, such as $H_2SO_4$, HCl, $HNO_3$, $H_2SO_3$, $HClO_4$ and $H_2CO_3$, to release the methylolphenol from the complex and dissolving the released methylolphenol in an organic solvent as hereinbefore defined such as kerosene, heptane, benzene, petroleum ether and the like. Generally, it is preferred to use about 0.1N to about 5N sulfuric acid to decompose the complex. According to this embodiment of the invention, the lithium-boron-methylolphenol complex is contacted with a dilute mineral acid to break the complex and release the methylolphenol. Preferably, the complex is treated with the dilute mineral acid in the presence of an organic solvent for the methylolphenol so that when the complex is decomposed the methylolphenol is dissolved in the organic solvent and the lithium and boron values of the complex are present in the aqueous phase as acids such as $H_3BO_3$ and acid salts such as $Li_2SO_4$. The organic phase, consisting of the methylolphenol solution, then is separated from the aqueous phase.

The organic solution thus recovered, which contains the methylolphenol, may be used as an extractant for recovering boron-values from boron-containing brines or for reducing the boron content of oil well brines, irrigation water and the like.

In order to illustrate the invention even more fully, the following specific examples are set forth. These examples are presented for illustrative purposes only and are not intended to limit the scope of the invention.

EXAMPLE I

A quantity of a methylolphenol solution containing about 10% by weight 2-bromo-4-tertiary-butyl-6-methylolphenol, about 10% by weight phenolic impurities and about 80% by weight benzene is mixed with a 0.5M aqueous solution of lithium metaborate. The lithium metaborate and 2-bromo-4-tertiary-butyl-6-methylolphenol are present in the mixture in a mole ratio of 0.67 moles lithium metaborate to 1 mole of the methylolphenol. The mixture is agitated for 4 hours at about 40°C. After a period of quiescence an aqueous phase-organic phase separation occurs and a solid complex of the lithium metaborate and the 2-bromo-4-tertiary-butyl-6-methylolphenol forms throughout the organic phase. The mixture then is filtered to recover the solid complex of lithium metaborate and 2-bromo-4-tertiary-butyl-6-methylolphenol.

EXAMPLE II

A 0.9M aqueous solution of lithium metaborate, prepared by dissolving stoichiometric quantities of lithium hydroxide monohydrate and boric acid, is contacted with an organic solution containing 4-phenyl-2,6-dimethylolphenol and phenolic impurities in a solvent comprising a mixture of kerosene, benzene and isopropyl ether, to provide a mole ratio of 0.8 mole lithium metaborate per mole of the dimethylolphenol. After mixing and settling an aqueous phase-organic phase separation occurs and a solid complex of the lithium metaborate and the 4-phenyl-2,6-dimethylolphenol is found throughout the organic phase. Substantially all of the phenolic impurities contained in the organic solution are soluble in the organic phase.

The mixture then is filtered to separate the solid complex of lithium metaborate and 4-phenyl-2,6-dimethylolphenol. The separated complex is mixed with dilute sulfuric acid and kerosene to dissolve the complex and form two phases, an organic phase containing the 4-phenyl-2,6-dimethylolphenol and an aqueous phase containing lithium and boron values. The organic phase then is separated and is recovered to provide an organic methylolphenol solution substantially free of phenolic impurities.

EXAMPLE III

A quantity of an organic methylolphenol solution containing about 15% by weight 2-methyl-4-tertiary-butyl-methylolphenol, about 5% by weight phenolic impurities and about 80% by weight kerosene is mixed with a 1M aqueous lithium metaborate solution according to the procedure described in Example I. The mixture, which contains about 0.67 mole of lithium metaborate per mole of methylolphenol, is agitated for 24 hours at about 25°C. After an aqueous phase-organic phase separation occurs, a solid complex of lithium metaborate and 2-methyl-4-tertiary-butyl-6-methylolphenol is found throughout the organic phase, with the phenolic impurities present in the methylolphenol solution remaining solubilized in the organic phase. The mixture is filtered to recover the solid complex of lithium metaborate and 2-methyl-4-tertiary-butyl-6-methylolphenol. Separation of the methylolphenol from the phenolic impurities contained in the organic methylolphenol solution thereby is effected.

EXAMPLE IV

A degraded methylolphenol solution containing 8.4% by weight of 2-chloro-4-(1,1,3,3-tetramethylbutyl)-6-methylolphenol, phenolic impurities, boron, sodium and potassium ions and a kerosene solvent is treated according to the process of the present invention to separate the methylolphenol values from the solution. A sample quantity of the degraded solution is washed successively with a 1/5-sample volume of 1N $H_2SO_4$, and two ½-samples volumes of 0.1N $H_2SO_4$ the aqueous phases being removed and discarded after each successive wash, to strip the boron, sodium and potassium values from the solution. About 625 ml. (500 gms.) of the washed solution are introduced into a container and contacted with 220 ml. (about 229 gms.) of a 1M aqueous solution of lithium metaborate for about 1 hour. The aqueous phase separates leaving a large mass of a solid lithium-boron-methylolphenol complex distributed throughout the organic layer. The solid-liquid mixture is separated by filtration. The solid phase lithium-boron-methylolphenol complex thus recovered weighs 164 gms. The filtrate is separated into an aqueous phase which weighs 166 gms. and an organic phase which weighs 365 gms.

An aliquot of the organic phase is mixed successively with a 1/5-aliquat volume of 1N $H_2SO_4$ and two ½-aliquat volumes of 0.1N $H_2SO_4$ with the aqueous phase being separated after each mixing. Analysis of the organic phase so treated shows it to contain only 1.07% by weight 2-chloro-4-(1,1,3,3-tetramethyl butyl)-6-methylolphenol. Thus, the crude, separated solid phase contains 90.7% of the 2-chloro-4-(1,1,3,3-tetramethyl butyl)-6-methylolphenol originally present in the degraded methylolphenol solution.

EXAMPLE V

A quantity of a degraded methylolphenol solution is stripped of its boron, sodium and potassium content according to the procedure described in Example IV. The resulting solution contains 8.6% by weight 2-chloro-4-(1,1,3,3-tetramethyl butyl)-6-methylolphenol, 10.8% by weight phenolic impurities (primarily ether- and methylene- dimer degradation products of the methylolphenol) and 80.6% by weight kerosene. A 1600 gram portion of this stripped extractant is mixed in a container with an aqueous solution of lithium metaborate, with a $LiB(OH)_4$ to methylolphenol mole ratio of 0.77 to 1. After allowing an aqueous phase-organic phase separation to occur, a precipitate begins to form throughout the organic phase within a few minutes. After about 20 hours the mixture is vacuum filtered and 581 grams of precipitate are recovered.

The precipitate thus recovered is mixed with 1N $H_2SO_4$ and 500 gm. kerosene and the mixture agitated until the precipitate is completely dissolved and two phases formed, an organic phase and an aqueous phase. The organic and aqueous phases are separated. Analysis of the organic phase shows it to contain 14.3 weight percent 2-chloro-4-(1,1,3,3-tetramethyl butyl)-6-methylolphenol and 3.3 weight percent phenolic impurities. Thus, the process of this invention is effective in recovering 87% of the methylolphenol content of the original degraded extractant and rejecting 84% of the phenolic impurities present in the degraded solution.

EXAMPLES VI, VII AND VIII

Three 80 gram samples of a stripped, degraded methylolphenol solution are treated to separate the methylolphenol content according to the procedure described in Example V in which the organic solution is mixed with an aqueous lithium metaborate solution to form a precipitate throughout the organic layer, the mixture is filtered to recover a solid phase, the solid phase is mixed with 1N $H_2SO_4$ and kerosene, and the methylolphenol content of the kerosene layer is determined. Each sample contains 9.8% by weight 2-chloro-4-(1,1,3,3-tetramethyl butyl)-6-methylolphenol in addition to phenolic impurities and a kerosene solvent. The test conditions and the results are set forth in the following table.

| Example No. | $LiB(OH)_4$ Concentration (M) | $LiB(OH)_4$ Methylol-phenol | Time (hrs) | Methylolphenol Recovery (%) |
|---|---|---|---|---|
| VI | 1 | .3 | 24 | 69 |
| VII | 1 | .5 | 24 | 88 |
| VIII | 0.2 | .5 | 96 | 86 |

As shown by a comparison between Examples VI and VII, a $LiB(OH)_4$ to methylolphenol mole ratio of below 0.5 is effective in complexing and precipitating a portion of the methylolphenol present in the original solution. However, the recovery of methylolphenol from the organic solution is relatively poor when the $LiB(OH)_4$ to methylolphenol mole ratio is below 0.5. Example VII shows that recovery of the methylolphenol is effected even when a dilute solution (0.2M) of lithium metaborate is used.

It will be understood, of course, that the above Examples are provided only to illustrate the invention, and that methylolphenols other than those described in the specific examples may be recovered from organic solutions by the process of the present invention.

While the present invention has been described with respect to what at present are considered to be preferred embodiments thereof, it will be understood that changes, substitutions, modifications and the like may be made therein without departing from the scope of the invention as defined in the claims.

What is claimed:
1. A method of separating methylolphenol from a phenolic impurity which comprises:
   contacting (A) an organic solution containing (1) an organic solvent; (2) at least one phenolic impurity and (3) about 1% to about 20% by weight of the methylolphenol having the formula

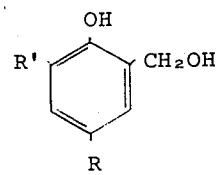

in which R is selected from the group consisting of hydrogen, phenyl, bromine, chlorine and alkyl radicals having from 3 to 8 carbon atoms and R' is selected from the group consisting of hydrogen, phenyl, chloro, CH₂OH and alkyl radicals having from 1 to 9 carbon atoms with (B) an aqueous alkaline borate solution containing lithium ions and being free of substantial amounts of other alkali metal ions, for a period of time sufficient for a solid complex of lithium and boron to form with said methylolphenol, the organic solution being contacted with said aqueous alkaline borate solution for at least about 0.5 hour at a temperature of between about 20° and about 40°C. and thereafter contacting said solid complex with a dilute inorganic acid and an organic solvent for said methylolphenol to dissolve said complex and provide an aqueous phase containing the lithium and boron values of said complex and an organic phase containing the methylolphenol portion of said complex and separating said phases, the concentration of lithium and boron ions in the alkaline borate solution being sufficient to provide at least about one lithium ion and one boron ion for every two moles of said methylolphenol in said organic solution;

said organic solvent being selected from the group consisting of benzene, toluene, xylenes, alkyl benzene, hexane, heptane, octane, nonane, kerosene, mineral spirits, petroleum ether, butyl ether, isopropyl ether, hexyl ethers, chloroform, carbon tetrachloride, chlorobenzene, monohydric alcohols having from 8 to 17 carbon atoms per molecule and mixtures thereof and said phenolic impurity being at least one member of the group consisting of a. unreacted starting materials having the formula

b. partially reacted starting materials having the formula

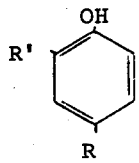

c. degradation products of the methylolphenol having the formula

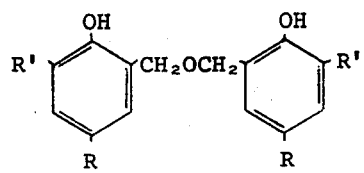

and d. degradation products of the methylolphenol having the formula

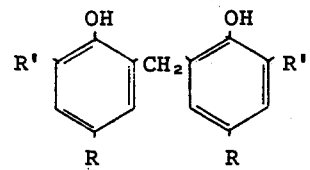

in which R and R' in each instance are as hereinbefore defined for the methylolphenol.

2. The method as defined in claim 1 in which said organic solution contains from about 1% to about 20% by weight methylolphenol, from about 1% to about 20% by weight of phenolic impurities, and from about 60% to about 98% by weight or an organic solvent for said methylolphenol.

3. The method as defined in claim 1 in which said aqueous alkaline borate solution comprises an aqueous solution of lithium metaborate.

4. The method as defined in claim 3 in which sufficient lithium metaborate is contacted with said organic solution to provide a lithium metaborate to methylolphenol mole ratio of at least about 0.5.

5. The method as defined in claim 4 wherein the methylolphenol is 2-chloro-4-(1,1,3,3-tetramethylbutyl)-6-methylolphenol.

6. The method as defined in claim 4 wherein the solvent is kerosene.

7. The method as defined in claim 1 in which said dilute organic acid comprises from about 0.1N to about 5N sulfuric acid.

8. The method as defined in claim 1 wherein the methylolphenol is 2-chloro-4-(1,1,3,3-tetramethylbutyl)-6-methylolphenol.

9. The method as defined in claim 8 wherein the organic solvent is kerosene.

* * * * *

UNITED STATES PATENT OFFICE
CERTIFICATE OF CORRECTION

PATENT NO. : 3,981,929
DATED : September 21, 1976
INVENTOR(S) : Robert E. Davis and Friedrich J. Weck It is certified that error appears in the above-identified patent and that said Letters Patent are hereby corrected as shown below:

The assignee should be Kerr-McGee Chemical Corporation.

Column 5, line 52, "$HClO_14$" should read -- $HClO_4$ --

Signed and Sealed this

Thirtieth Day of November 1976

[SEAL]

Attest:

RUTH C. MASON
Attesting Officer

C. MARSHALL DANN
Commissioner of Patents and Trademarks